US011197612B2

(12) United States Patent
Costantine et al.

(10) Patent No.: US 11,197,612 B2
(45) Date of Patent: Dec. 14, 2021

(54) NON-INVASIVE BIOLOGICAL, CHEMICAL MARKERS AND TRACERS MONITORING DEVICE IN BLOOD INCLUDING GLUCOSE MONITORING USING ADAPTIVE RF CIRCUITS AND ANTENNA DESIGN

(71) Applicant: AMERICAN UNIVERSITY OF BEIRUT, Beirut (LB)

(72) Inventors: Joseph Costantine, Albuquerque, NM (US); Rouwaida Kanj, Portland, OR (US); Assaad Eid, Paris (FR)

(73) Assignee: American University of Beirut, Beirut (LB)

(*) Notice: Subject to any disclaimer, the term of this patent is extended or adjusted under 35 U.S.C. 154(b) by 434 days.

(21) Appl. No.: 16/152,990

(22) Filed: Oct. 5, 2018

(65) Prior Publication Data

US 2019/0104939 A1  Apr. 11, 2019

Related U.S. Application Data

(60) Provisional application No. 62/568,658, filed on Oct. 5, 2017.

(51) Int. Cl.
*A61B 5/145* (2006.01)
*A61B 5/00* (2006.01)
(Continued)

(52) U.S. Cl.
CPC .......... *A61B 5/0024* (2013.01); *A61B 5/0507* (2013.01); *A61B 5/14532* (2013.01); *H01Q 1/2291* (2013.01); *H01Q 1/273* (2013.01); *H01Q 3/24* (2013.01); *H01Q 3/26* (2013.01); *H01Q 5/30* (2015.01); *H01Q 7/00* (2013.01);
(Continued)

(58) Field of Classification Search
CPC ......... A61B 5/05; A61B 5/0507; A61B 5/145; A61B 5/14532; A61B 5/6801; A61B 5/6802; A61B 5/6813; A61B 5/6824; A61B 2562/0223; A61B 2562/0228
See application file for complete search history.

(56) References Cited

U.S. PATENT DOCUMENTS 8,029,443 B2   10/2011   Goodnow ..................... 600/365
8,135,450 B2    3/2012   Esenaliev et al. ............ 600/316
(Continued)

FOREIGN PATENT DOCUMENTS

| GB | 2428093 A | 1/2007 | |
| WO | 2010/033724 | 3/2010 | ............. G01N 27/26 |
| WO | 2016/080911 | 5/2016 | ............. A61B 5/145 |

OTHER PUBLICATIONS

Baca, JT, et al., "Tear Glucose Analysis for the Noninvasive Detection and Monitoring of Diabetes Mellitus," The Ocular Surface, vol. 5, No. 4, pp. 280-293, (Oct. 2007).
(Continued)

*Primary Examiner* — Eric F Winakur
(74) *Attorney, Agent, or Firm* — J. Peter Paredes; Amin Talati Wasserman LLP

(57) ABSTRACT

The device measures glucose concentration in blood without any extraction of blood. The device is a non-invasive method for measuring glucose Radio Frequency and Antenna Circuits and Systems. The device is a wearable device that can non-invasively measure blood glucose levels in an instantaneous manner and continuous manner.

20 Claims, 15 Drawing Sheets

(51) Int. Cl.
H01Q 1/22 (2006.01)
H01Q 1/27 (2006.01)
H01Q 3/24 (2006.01)
H01Q 7/00 (2006.01)
H01Q 5/30 (2015.01)
H01Q 21/20 (2006.01)
H01Q 21/00 (2006.01)
H01Q 21/06 (2006.01)
H01Q 21/28 (2006.01)
H01Q 3/26 (2006.01)
A61B 5/0507 (2021.01)

(52) U.S. Cl.
CPC ....... *H01Q 21/0037* (2013.01); *H01Q 21/065* (2013.01); *H01Q 21/20* (2013.01); *H01Q 21/28* (2013.01); *A61B 5/1451* (2013.01); *A61B 5/14546* (2013.01); *A61B 2562/046* (2013.01)

(56) References Cited

U.S. PATENT DOCUMENTS

| | | | |
|---|---|---|---|
| 8,615,282 B2 | 12/2013 | Brister et al. ................. | 600/345 |
| 9,247,905 B2 | 2/2016 | Caduff et al. ........ | A61B 5/4869 |
| 9,282,925 B2 | 3/2016 | Kamath et al. .... | A61B 5/14865 |
| 9,526,431 B2 | 12/2016 | Zakharov et al. . | A61B 5/14551 |
| 9,572,523 B2 | 2/2017 | Boock et al. ...... | A61B 5/14865 |
| 9,700,250 B2 | 7/2017 | Min et al. ............ | A61B 5/1473 |
| 9,750,460 B2 | 9/2017 | Goode et al. ........ | A61B 5/7203 |
| 2003/0036674 A1 | 2/2003 | Bouton ........................... | 600/12 |
| 2008/0319285 A1 | 12/2008 | Hancock ....................... | 600/309 |
| 2010/0099973 A1 | 4/2010 | Goodnow ..................... | 600/365 |
| 2010/0112614 A1* | 5/2010 | Axelrod .................. | C12Q 1/54 435/14 |
| 2013/0303868 A1* | 11/2013 | Fischer .............. | A61B 5/14532 600/364 |
| 2016/0051171 A1 | 2/2016 | Pikov et al. ........ | A61B 5/14532 |
| 2016/0317070 A1 | 11/2016 | Sivaraman et al. ......................... | A61B 5/14532 |
| 2017/0181658 A1 | 6/2017 | Dettmann et al. ... | A61B 5/0507 |

OTHER PUBLICATIONS

Caduff, A. et al., "Non-invasive glucose monitoring in patients with Type 1 diabetes: A Multisensor system combining sensor for dielectric and optical characterization of skin," Biosensor and Bioelectronics 24, pp. 2778-2784 (2009).

Caduff, A. et al., "Multisensor Concept for non-invasive Physiological Monitoring," Instrumentation and Measurement, Technology Conference—IMTC 2007 Warsaw, Poland, pp. 1-4 (May 1-3, 2007).

Cano-Garcia, H, et al. "Reflection and Transmission Measurements Using 60 GHz Patch Antennas in the Presence of Animal Tissue for non-Invasive Glucose Sensing," 2016 10th European Conference on Antennas and Propagation (EuCAP), pp. 1-3 (Apr. 2016).

Elsheakh, D et al., "Non-Invasive Electromagnetic Biological Microwave Testing," Microwave Systems and Applications, Sotirios K. Goudos, IntechOpen, DOI: 10.5772/64773; https://www.intechopen.com/books/microwave-systems-and-applications/non-invasive-electromagnetic-biological-microwave-testing, pp. 276-317 (Jan. 11, 2017).

Goh, J. et al., IFMBE Proceedings, vol. 52, 7th WACBE World Congress on Bioengineering 2015, pp. 1-234 (Jul. 6-8, 2015).

Muhamed, R., "Direction of Arrival Estimation Using Antenna Rays," Thesis submitted to Faculty of the Virgina Polytechnic Institute and State University, pp. 1-175 (Jan. 1996).

Oliver, NS, et al. "Glucose sensors: a review of current and emerging technology," Diabetic Medicine, vol. 26, No. 3, pp. 197-210 (2009).

Saha, S., et al. "Evaluation of the Sensitivity of Transmission Measurements at Millimeter Waves using Patch Antennas for Non-invasive Glucose Sensing," 2016 10th European Conference on Antennas and Propagation (EuCAP), pp. 1-4 (Apr. 2016).

PCT Search Report and Written Opinion issued in corresponding foreign application, PCT/US2018/054627 pp. 1-7 (dated Jan. 31, 2019).

* cited by examiner

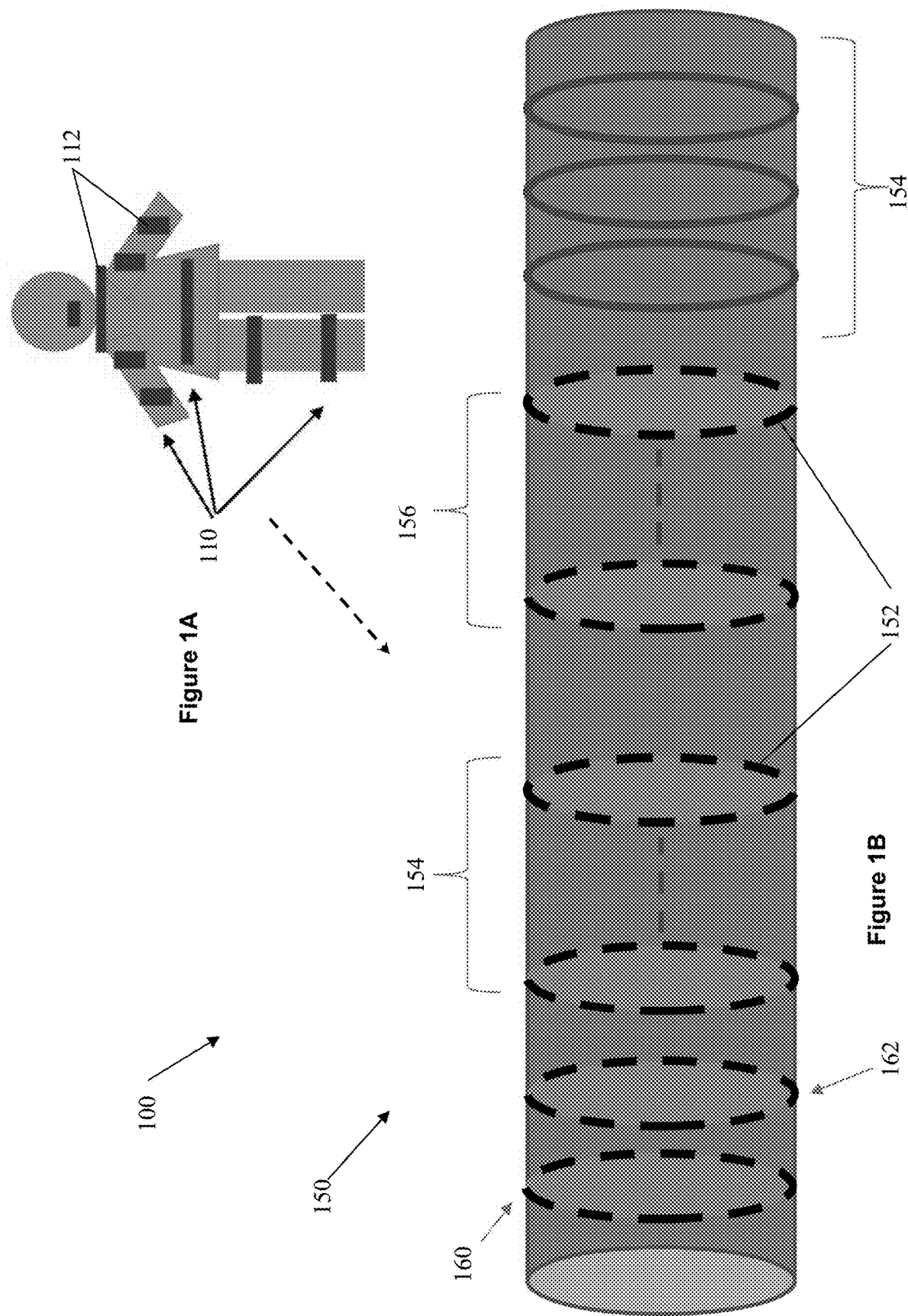

Directivity = 31.55 dBi

Array Pattern directivity — Example for ($\theta=60$, $\phi=0$)

Array Pattern directivity — Example for broadside steering ($\theta=0$, $\phi=0$)

NON-INVASIVE BIOLOGICAL, CHEMICAL MARKERS AND TRACERS MONITORING DEVICE IN BLOOD INCLUDING GLUCOSE MONITORING USING ADAPTIVE RF CIRCUITS AND ANTENNA DESIGN

CROSS-REFERENCE TO RELATED APPLICATIONS

The present application claims priority from U.S. provisional application Ser. No. 62/568,658, filed Oct. 5, 2017, herein incorporated by reference in its entirety.

BACKGROUND

The invention generally relates to systems and methods for processing data received from a sensor.

Diabetes Mellitus (DM) is increasing worldwide at an unprecedented pace. The International Diabetes Federation (IDF) estimates an upsurge from 382 million diabetics in 2013 to 592 million diabetics by 2030. The World Health Organization has declared it as a global epidemic. The annual cost with diabetes management will increase from an approximate $376 billion in 2013 to $490 billion in 2030. The management of DM involves strict glycemic control with a target HbAlc of 7% to reduce complications. Self-monitoring of blood glucose and self-knowledge of daily blood glucose increase compliance to medications and lifestyle measures and present higher chances of achieving a target HbAlc. Self-monitoring of blood glucose is also important in patients with type 1 diabetes who are at high risk of hypoglycaemia unawareness so that appropriate action can be taken on time. The normal blood glucose concentrations are in the range of 4-8 mmol/L whereas pathophysiological blood glucose concentrations are in the range of 2-30 mmol/L in patients with DM.

Currently monitoring of blood glucose concentrations is mainly done by self-monitoring blood glucose (SMBG) systems which involves the users pricking their fingers for each estimation. Continuous glucose monitoring systems (CGMS) are also used to monitor blood glucose especially for patients on insulin pumps. Almost all SMBG systems use a cost effective electrochemical biosensor and they suggest automatic lancet devices to prick the fingers to obtain the blood samples which can be painful as patients with DM require to monitor blood sugars very frequently up to 4-7 times daily. The CGMS system although minimally invasive suffers from limitations in terms of discomfort to patients, the requirement for continuous calibration and high susceptibility to biofouling. Current techniques for self-blood glucose monitoring tend to be invasive, painful and high cost.

CGMS was introduced as a minimal invasive solution, utilizing interstitial fluid (ISF) to estimate blood glucose (BG) values. This invasive technology is widely accepted and extensively used by type 1 and type 2 diabetics to continuously monitor their blood glucose levels on a daily basis. The present invention attempts to solve these problems as well as others.

SUMMARY OF THE INVENTION

Provided herein are systems, methods and apparatuses for a Non-Invasive Biological, Chemical Markers and Tracers Monitoring device in blood including Glucose Monitoring Using RF Circuits and Antenna Design. The Monitoring Device generally comprises: a body area network operably coupled to a plurality of device antenna arrays; the body area network comprised of a plurality of sensors and the plurality of device antenna arrays comprise a plurality of circular antenna arrays; each circular antenna array comprises a first set of antenna arrays that operate at a mm-wave range and a second set of antenna arrays operates at a microwave range; at least two antenna elements are placed symmetrically opposite on a circular circumference of the device at a microwave range; the plurality of device antenna arrays further comprises a filter element and a coupler including a functionality sensitive to a medium.

A method of monitoring is disclosed and generally comprises: operably coupling a body area network to a plurality of device antenna arrays; the body area network comprised of a plurality of sensors and the plurality of device antenna arrays comprise a plurality of circular antenna arrays; operating each circular antenna array with a first set of antenna arrays at a mm-wave range and operating a second set of antenna arrays at a microwave range; placing at least two antenna elements symmetrically opposite on the circular circumference of the device at a microwave range; including a filter element and a couple with a functionality sensitive to a medium.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 1A is a body area network comprised of one, two or multiple sensors. The body area network will collect information from the different sensor locations optimally chosen based on patient specific vein detection. The data from the different sensors will allow to model glucose monitoring while ruling out error due to misreading in one of the sensors, field fail of one of the sensors, or outliers, thereby preserving reliability of the design.

FIG. 1B is a schematic showing one component or system.

DETAILED DESCRIPTION OF THE INVENTION

Figure 2A:
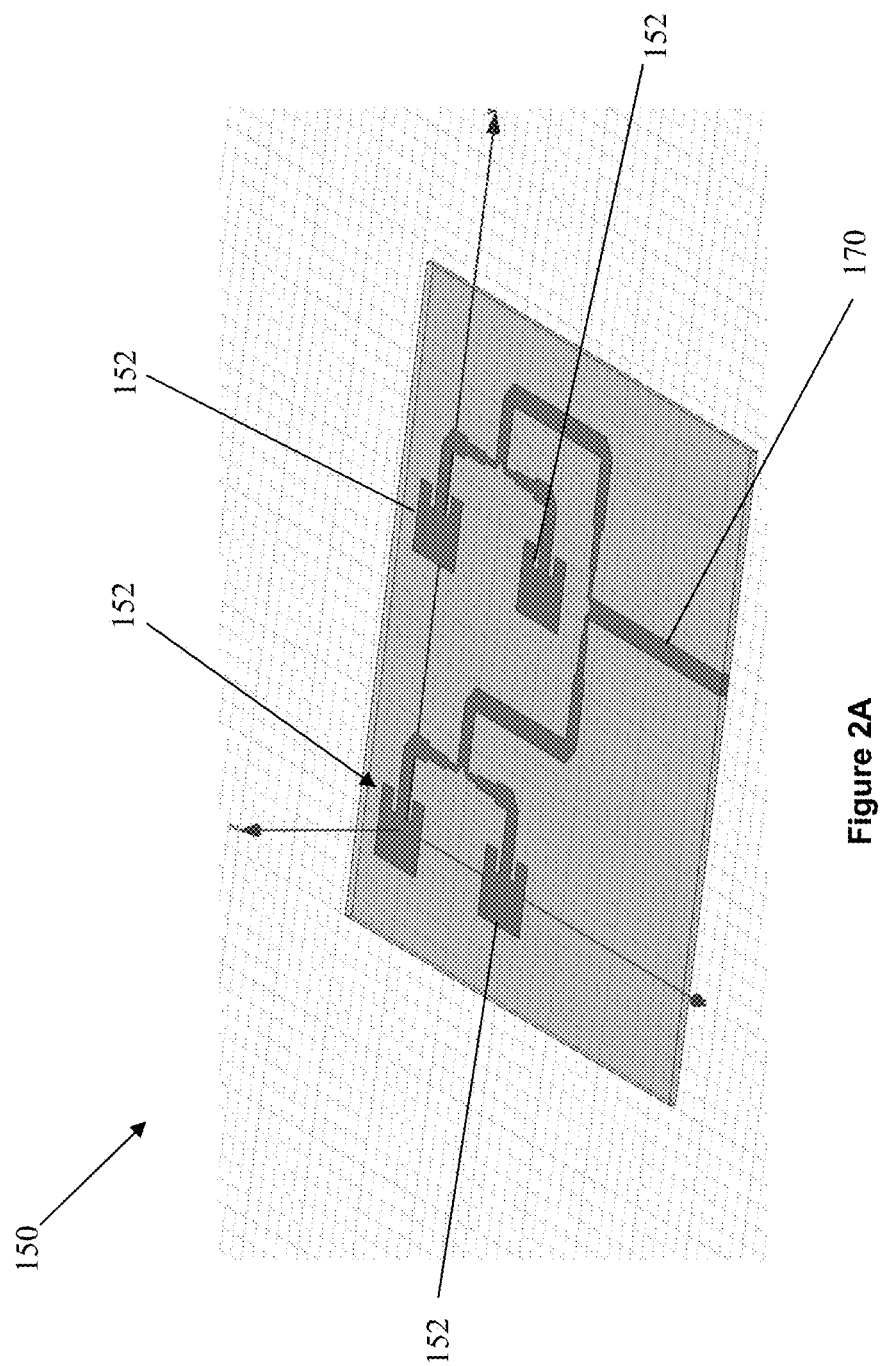
FIG. 2A is a perspective view of an Antenna Array with 4 elements, according to one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument pointing to the outside of the body when the instrument is being used. A distal end refers to the end of a component further from the operator and touching towards the monitored area of a patient body.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The invention measures biological and chemical molecules and markers such as glucose concentration in blood without any extraction of blood. It is a non-invasive method for measuring glucose using radio frequency and antenna circuits and systems. The body area network can be comprised of a plurality of monitoring devices. A monitoring device can be a wearable gadget such as a watch, a bracelet, a necklace, an anklet, a sleeve or other; this gadget will non-invasively measure blood molecules/markers. The devices are connected to a computing system which provides feedback based on other sensors to adjust device measurements, collect more data, and then based on these measurements the computing system report the glucose levels in an instantaneous and continuous manner. The computing system due to the component redundancy and multichannel readings has the ability to detect outlier channels and hence provide more reliable readings.

None of the prior solutions offers a continuous radiofrequency (RF) and antenna-based noninvasive glucose monitoring; a plethora of antenna array solutions for heightened accuracy; a plethora of radiation frequencies that vary from Ultra High Frequency (UHF) to mmwave in one single device for heightened accuracy; the RF and antenna design functionality is robust and sweat tolerant; multitude of wearable options; adaptive beam steering and adaptive power levels based on patient specific vein detection; adaptive beam steering for multiple readouts from an individual antenna set, redundancy in elements, and outlier detection solutions based on a body area network, and RF-devices like the coupler, and banks of filters contribute with an additional capability for more accurate functionality.

A device for continuously measuring biological, chemical markers and other tracers in the blood stream for physiological and pathophysiological screening in health and in disease in a non-invasive manner. Biological markers can include novel/foreign/malignant or non-malignant cells or other newly developed molecules that may not be part of the typical constituents of the biological system. Markers can also be traced not only in blood, but in the rest of the biological system, such as saliva, tissue, and the like.

Markers as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Markers can include naturally occurring substances, artificial substances, metabolites, and/or reaction products. In some embodiments, the Marker for measurement by the sensor heads, devices, and methods is a marker. However, other markers are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute markers in certain embodiments. The markers can be naturally present in the biological fluid, for example, a metabolic product, a hormone, an antigen, an antibody, and the like. Alternatively, the marker can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated markers. Markers such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

An example of pathophysiological alteration leading to diseases include, but are not limited to, hyperglycemia/diabetes, cholesterolemia, heart disease markers as well as other biological alterations that involve measuring variations of glucose level, cholesterol levels, Pro-BNP (pro-Brain Natriuretic peptide) and troponin levels, and other molecular markers in living tissue. For example in diabetes, the proposed prototype is envisioned to help monitor instantaneous glucose levels to be used: to determine the alteration in glycemia and variations from norm; and for autonomous interventions such as insulin injections; and to offer diabetic patients an improved and self-constrained control of the disease. Thus, along with an estimate of the bulk concentration, the device monitors the rate of change of concentrations to predict possible hyperglycemia and hypoglycemia early.

The device or component will encompass a plurality of components arranged to establish a body area network coverage. The network will correlate different measurements from different locations on the human body. Measurements will be taken simultaneously from a plurality of locations on the human body by a plurality of components at a plurality of frequencies and locations. All results will be communicated to a wearable central unit that will correlate the data together in order to come up with an accurate estimate. The human body may be an anatomical limb, digital, or extremity.

Different components of the body area network may include a bracelet, necklace, anklet, ring, sleeve, belt, leg braces, teeth guards, neck braces, shoe wraps, socks, underwear, shirts, hats, watches, glasses, stick or patch devices, or other forms of wearables whether clothing or medical device based. Redundancy and plurality of components can improve accuracy and increase overall reliability of the system. The components will enable measurements of different depths. In one embodiment, a belt targets abdominal measurements. The belt component can be featured with a loop antenna of multiple turns to satisfy the length requirements.

Each component of the device comprises a plurality of antenna arrays, single antenna elements, loop antennas, filtennas and microwave devices such as couplers and filters or banks of antennas, filters and other RF devices to capture the response at different frequency bands. The device will also include filters and couplers whose functionality is operational at the various frequency bands from Ultra High Frequency (UHF) through microwave to Ka-band and mm-wave, where these devices will operate independently, jointly, consequently, or in response to marker measurements. To save power, some components of the device or the body area network may be dormant, others may be active until an alert, sudden change in measurement is reported either to large fluctuation of body markers, or due to defect happening in one of the device components . . . etc. Sufficient number of device components will be operable at any time to guarantee accuracy and good correlation with invasive measurements. This may depend on patient physiology. In one embodiment, band pass or band reject filters are operably coupled to the device. In one embodiment, narrow band hybrid couplers independent of the antenna bands are employed. In one embodiment, some of the devices are hybrid structures that combine various microwave components together such as filtenna structures (a filter-antenna module). In one embodiment, the structural built involves antenna arrays. The device consists of a plurality of antenna arrays that can be circular, planar, or linear. Multiple antenna arrays are arranged in circular platform for best fitting of the human body topology. Each array has at least two elements. All of the device measurements will be independent of each other or pooled into a comprehensive measurement. The data collected will be analyzed and correlated together in a central processing unit.

The RF device arrangements are applied against living tissue. The device will emit an EM wave that can be reflected by or transmitted through the human tissue. The device will detect both the reflected and the transmitted waves from any type of tissue, including, but not limited to: dry skin, wet skin, muscle, blood, nervous tissue; fingernails, hair, fatty tissue, and the like. Other device arrangements, like filters or banks of filters, the signal will be affected by the impedance change of the human body.

In one embodiment, single antenna elements are designed to be reconfigurable to change frequency of operation, polarization, radiation pattern or a combination of the above. The change frequency of operation, polarization, radiation pattern is achieved using electrical or digital switches such as pin diodes, radio frequency microelectromechanical systems (RF MEMs), varactors, or DTC (digital tunable capacitors). In one embodiment, the spacing physically, mechanically, and/or electrically using, for example, active electronic elements.) is varied between antenna elements of the array to control radiation pattern, which can be predetermined or tunable during runtime or realtime.

A radio frequency microelectromechanical system (RFMEMS) is a microelectromechanical systems with electronic components comprising moving sub-millimeter-sized parts that provide radio frequency functionality. RF functionality can be implemented using a variety of RF technologies. Besides RF MEMS technology, III-V compound semiconductor (GaAs, GaN, InP, InSb), ferrite, ferroelectric, silicon-based semiconductor (RF CMOS, SiC and SiGe), and vacuum tube technology are available to the RF designer. Each of the RF technologies offers a distinct trade-off between cost, frequency, gain, large-scale integration, lifetime, linearity, noise figure, packaging, power handling, power consumption, reliability, ruggedness, size, supply voltage, switching time and weight.

A "varactor" is a digitally tuned capacitor is an IC variable capacitor based on several technologies, either MEMS, BST and SOI/SOS devices and vary in capacitance range, quality factor and resolution for different RF tuning applications. MEMS devices have the highest quality factor and are highly linear, and therefore are suitable for antenna aperture tuning, dynamic impedance matching, power amplifier load matching and adjustable filters. BST device are based on Barium Strontium Titanate and vary the capacitance by applying high voltage to the device. The tuning accuracy is limited only by the accuracy of the D-A converter circuitry that generates the high voltage. SOI/SOS tuning devices are constructed as solid state FET switches built on insulated CMOS wafers and use MIM caps arranged in binary-weighted values to achieve different capacitance values. SOI/SOS switches have high linearity and are well suited to low power applications where high voltages are not present. The capacitance values are designed for antenna impedance matching in multi-band that operate over wide frequency ranges.

The device comprises a signal generation circuit connected to device components in order to generate a signal voltage. Additionally, it comprises a plurality of measuring circuits that will capture the reflected and transmitted responses.

The Array components feature beam steering capabilities to scan an area of the skin and underlying tissue and body fluids. The beam steering capabilities enable local spatial variation in the measurement, while the full body network, provides global spatial variation and allows different antenna elements to receive different components of the signal based on the tuning. The beam steering range is also based on the vein imaging to target dense areas.

Both array and single antennas will operate at different input power levels, at the various frequency bands of operation. Vein depth information is used to vary signal power level. This feature is controlled by the central unit.

Optical or infrared sensors for vein recognition capability will be added to the device. Without loss of generality, any form of vein detection via image processing can be utilized. The terms 'sensors,' and 'sensing mechanism' as used herein are broad terms, and are to be given their ordinary and customary meaning to a person of ordinary skill in the art (and are not to be limited to a special or customized meaning), and refer without limitation to the region or mechanism of a monitoring device responsible for the detection of a particular marker. The sensor goal is to identify the proper depth and location of capillary networks. The feedback is sent to a central processor which in turn uses algorithms to help derive optimal beam steering patterns and power intensity levels for best coverage of key sensitive locations. Its goal is also to identify the depth of the vein to determine the optimal power level ranges. The captured reflected and transmitted responses will be correlated together to determine the concentration of a given molecule/marker (e.g. glucose) in the blood. To derive said blood disease level such glucose level, from a combination of at least said first, second and third electric parameter groups and wherein said control unit is structured and adapted to determine said glucose level from all of the following parameters (listed in the following slides).

In one embodiment, the optical sensor comprises a vein tracking system including an NIR source operably coupled to a NIR sensitive camera, which is operably connected to a processor. In one embodiment, the vein tracking system comprises an 880 nm Near Infrared and CMOS Sensor with Maximum Curvature Points Segmentation. In another embodiment, charge-coupled device (CCD) sensors are used instead of the CMOS sensor for more accuracy. CCD images are clearer and do not need image processing. The image will be processed and the antenna may be placed to optimally target a single or multiple locations of dense capillaries. Accordingly, a predetermined range of angles θ for the optimal Beam steering will be determined, as shown in FIG. 2B. The predetermined range will take into consideration margins for error in distance estimations h and di, and the like. In one embodiment, the distance di may be adjusted based on specific knowledge of the anatomy of the patient. The antenna is placed at a distance h from the skin, and then the prescreened image will determine the optimal placement of the antenna to target multiple veins/capillaries and determine the angle range for the sweeping of the beam to measure from multiple locations. This step is recalibrated as vein locations can change based on certain diseases and seasons and the like. Localization is important because in obese people and kids it is often difficult to detect the veins.

The power level at skin should meet SAR (Specific absorption rate) requirements according to Table 1

TABLE 1

| f [GHz] | $SAR_{max}$ [W/kg] |
|---|---|
| 3 | 0.098 |
| 6 | 0.80 |
| 24 | 7.74 |
| 77 | 27.2 |
| 100 | 33.9 |

Given: Pin of the antenna the following relations hold:

Pr=Pin (PR is the radiated power=input power assuming perfect antenna "Pin")

P0=Pr*$e^{-\alpha\_air(\|h/\cos\theta\|)}$ (distance between antenna and skin with beam angle θ assuming air separates antenna and skin).

P0<SAR (Specific absorption rate).

Critical values below SAR maybe identified based on sensitivity analysis of proposed designs. If the intensity of the transmitted power is changed, then the power amplifier of the transmitter RF chain must be reconfigurable and adjusted accordingly.

In one embodiment, the linear Array is an array of antenna elements in linear arrangement. The linear array can result in a main beam whose direction is determined by (θ, φ), as shown in FIG. 2C, and based on the per-element excitation amplitude ($a_i$) and phase ($knd_x u_i$) according to the pattern multiplication listed below:

Array Pattern=Element Pattern×Array Factor $$F(u, v) = f(u, v) \sum_{n=-(N-1)/2}^{(N-1)/2} a_n e^{jknd_x u} = f(u, v) F_A(u) \quad \text{Equation (1)}$$

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

In one embodiment, tuning the power is done in sync with beam steering capabilities, and array spacing, based on desired transmission location. The beam steering enables scanning of variable depths and breadth spatial variations. Tuning the power allows to capture proper depth of targeted areas response. Multiple power level readings increase the accuracy, target the specific depth of the veins addressed which is adjusted based on patient requirements within SAR, and help obtain more accurate readings according to the local spatial variations, which will be done for proper coverage at frequencies that target different depths including both blood and interstitial fluids regions. Hence, the depth targets patient specific and multi-layer coverage locally. The whole body network will provide measurements based on wide range spatial variations.

The device components monitor the changes in the blood dielectric properties, bodily fluids or tissue and responds to the permittivity changes by altering its radiation characteristics.

Additionally the device will communicate the results to web based and electronic medical record registries and systems, accessible by physicians and hospital caregivers. The device will communicate the results to an integration/analysis device, such as a mobile phone, a telemedicine or a home-health kit, where the information will be recorded and analyzed.

The RF device arrangements are applied against living tissue. A signal generation circuit is connected to device components in order to generate a signal voltage, and a plurality of measuring circuits will capture the response of said tissue.

The signal and its response will operate at least at a first frequency for measuring a first group of electric parameters in the microwave frequency range. The signal and its response will also operate at a second frequency for measuring a second set of electric parameters at the mm-wave frequency range. The signal and its response will operate at a third frequency for measuring a third set of electric parameters at the UHF frequency range. In one embodiment, the first frequency is between about 1 GHz and about 8 GHz, and the mm-wave frequency between about 30 GHz and about 300 GHz, and UHF frequency between about 100 MHz-about 1000 MHz. In alternative embodiments, additional components from the K- and KA-bands covering about 18-about 27 GHz and about 26.5 GHz-about 40 GHz may be added to the device.

To derive said blood disease level such glucose level, from a combination of at least said first, second and third electric parameter groups and wherein said control unit is structured and adapted to determine said glucose level from all of the following parameters (listed in the following discussion.

The device will communicate the results to a personal mobile device such as a phone where the information will be recorded and analyzed over a certain period of time to personally assess the patient's state and condition. The phone or mobile device may be incorporated into an android/iOS application. The device and system will send notification for alarming situations.

Additionally, the device will communicate the results to a central web based electronic medical record registry and system, that is accessible to physicians and hospital care givers. The recording of the measurements directly in the electronic medical records of the patient as well as them being only monitored by medical personnel and then recorded.

The Monitoring Device 100 comprises a body area network 110 operably coupled to a plurality of device antenna arrays 150. The body area network 110 comprised of a plurality of sensors 112 as shown in FIG. 1A. The plurality of device antenna arrays 150 is shown in FIG. 1B and the plurality of device antenna arrays 150 comprises a plurality of circular antenna arrays 152. In one embodiment, the plurality of circular antenna arrays 152 is arranged in circular fashion. Each circular antenna array comprises a first set of antenna arrays 154 that operate at the mm-wave range and a second set of antenna arrays 156 operates at microwave range. A pair of antenna elements placed symmetrically opposite on the circular circumference of the device at microwave range. The plurality of device antenna arrays 150 further comprises a filter element 160 and a coupler 162 whose functionality is sensitive to the medium as well. These devices will operate independently or jointly. The plurality of device antenna arrays 150 further comprises an array of loop antennas 164 at the UHF range whether uniform or following an array distribution including distribution parameters.

Figure 2B:
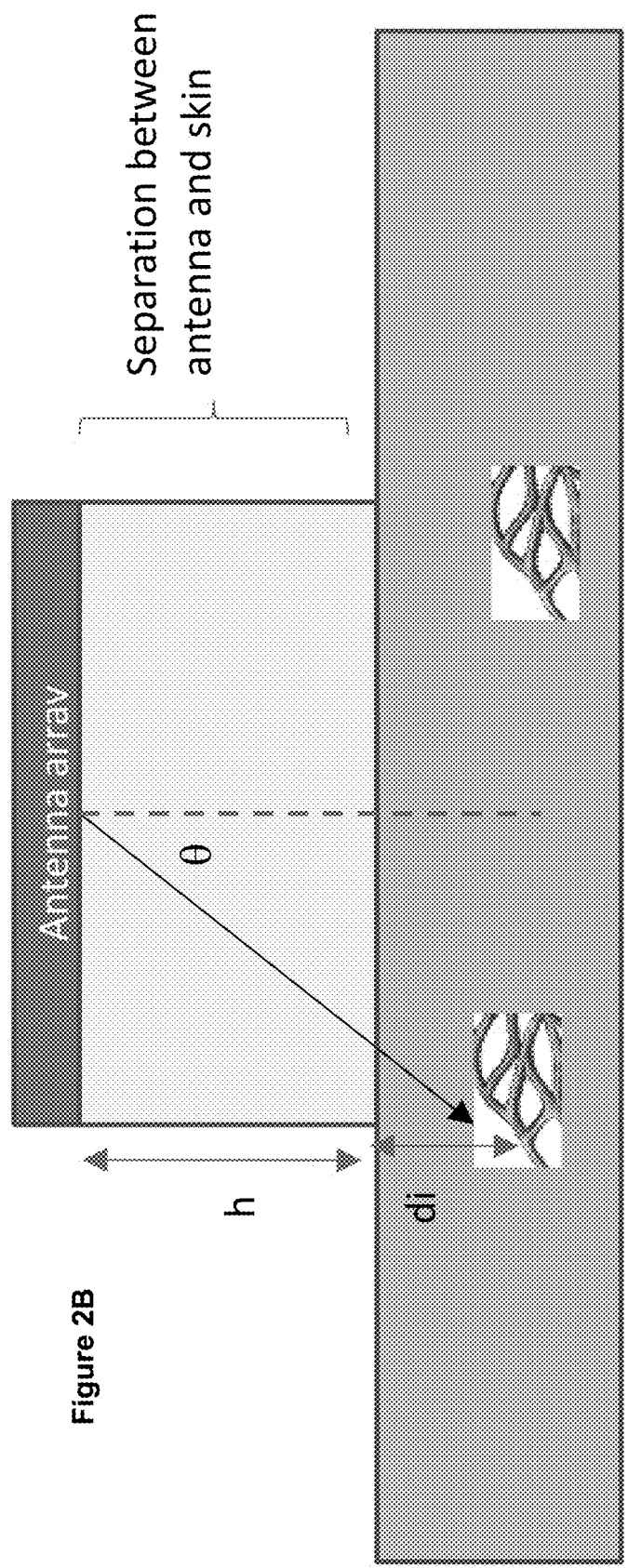
FIG. 2B is a schematic showing the angle θ for the optimal Beam steering and the distance h signifying the separation between the antenna and skin.
Figure 2C:
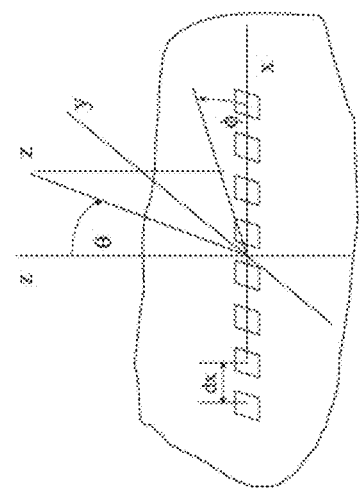
FIG. 2C is a diagram of an array of antenna elements in linear arrangement result in a main beam whose direction is determined by (θ, ϕ).

As shown in FIG. 2, an embodiment of the plurality of device antenna arrays 150 includes at least 4 circular antenna arrays 152 operating at about 60 GHz and operably coupled to a waveguide based feeding network 170. Alternatively, the plurality of device antenna arrays 150 includes 4 or more circular antenna arrays 152 operating at about 60 GHz. Alternatively, the plurality of device antenna arrays 150 includes less than 4 circular antenna arrays 152 operating at about 60 GHz.

Figure 3:
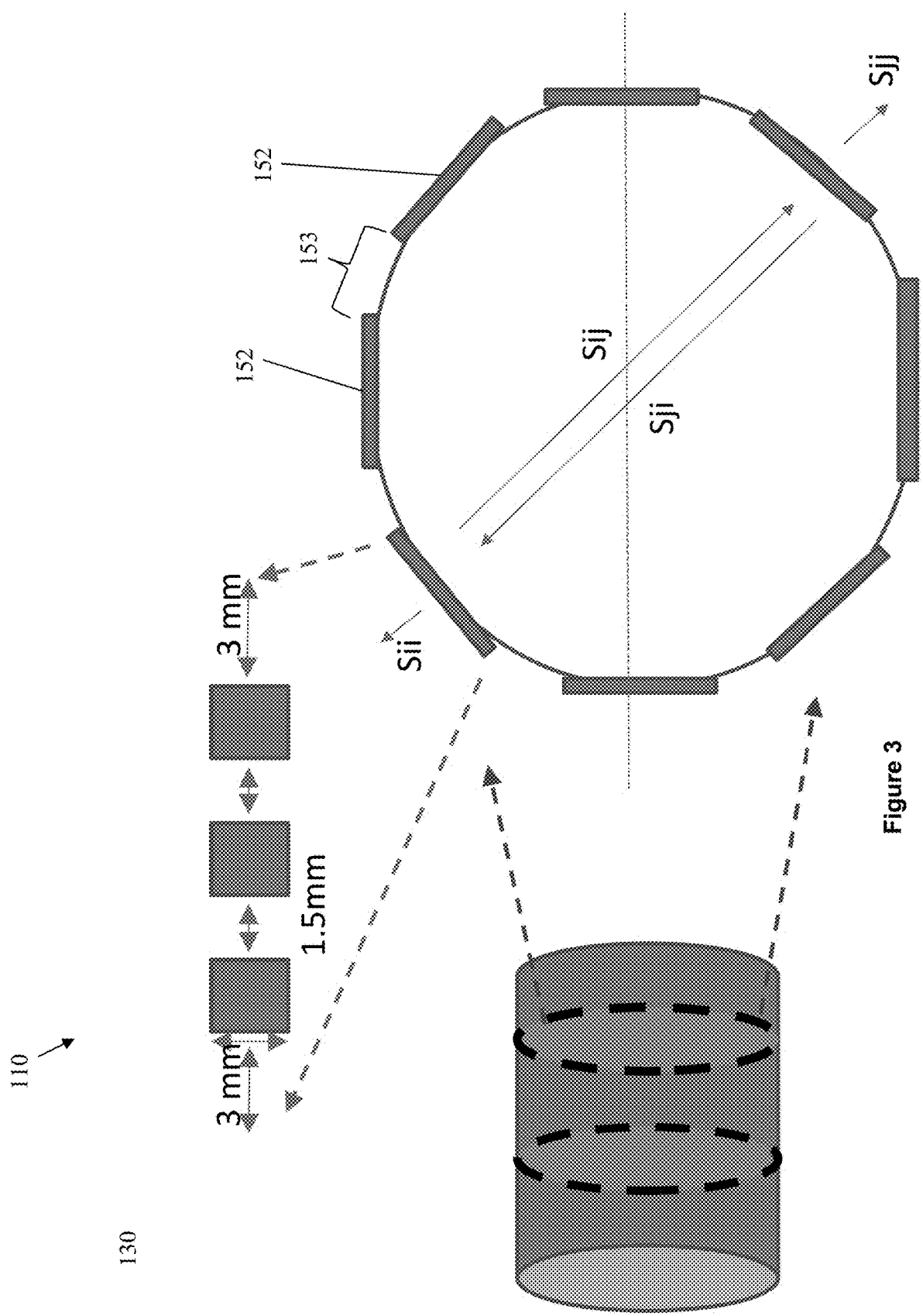
FIG. 3 is a schematic showing an mm-wave Antenna Arrays arrangement, according to one embodiment.

In one embodiment, the plurality of device antenna arrays 150 comprises at least three elements allowing for at least 8 antenna arrays 152 to wrap around a limb or the human hand in the arrangement shown in FIG. 3. In other embodiments, less than 8 antenna arrays wrap around a limb or human hand, and in other embodiments more than 8 antenna arrays wrap around a limb or human hand. In the same embodiment, the spacing 153 between the antenna array elements is about a half wavelength enabling good beam directivity which is also good for maximal transmission at a diametrically opposite antenna array. In one embodiment, the beam directivity is at least about 31.55 dBi, in other embodiments, the beam directivity is less than about 31.55 dBi, and in other embodiments the beam directivity is greater than about 31.55 dBi.

Directivity is a parameter of an antenna or optical system which measures the degree to which the radiation emitted is concentrated in a single direction. It measures the power density the antenna radiates in the direction of its strongest emission, versus the power density radiated by an ideal isotropic radiator (which emits uniformly in all directions) radiating the same total power. An antenna's directivity is a component of its gain; the other component is its (electrical) efficiency. Directivity is an important measure because many antennas and optical systems are designed to radiate electromagnetic waves in a single direction or over a narrow angle. Directivity is also defined for an antenna receiving electromagnetic waves, and its directivity when receiving is equal to its directivity when transmitting.

The antenna arrays 152 operate at mm-wave and each antenna array operates at a different channel within the mm-wave. In one embodiment, a first antenna array operates at about a 60 GHz, a second antenna array operates at about a 60.1 GHz, a third antenna array operates at about 60.2 GHz, a fourth antenna array operates at about a 60.3 GHz, a fifth antenna array operates at about a 60.4 GHz, a sixth antenna array operates at about a 60.5 GHz, a seventh antenna array operates at about 60.6 GHz, and an eighth antenna array operates at about 60.7 GHz. In one embodiment, the antenna arrays 152 operate at a different channel separated by at least about 0.05 GHz, alternatively, the antenna arrays 152 operate at a different channel separated by at least about 0.10 GHz. In another embodiment diametrically opposite arrays transmit signals to each other and will operate at the same channel, leading to 4 exclusive channels for the above example. In a third embodiment, elements that are neighboring transmitting/receiving array will be able to capture the coupled electromagnetic field.

In one embodiment, waveguide based feeding networks are utilized, which can be uniformly fed and can follow a certain distribution. In one embodiment, following parameters are utilized. P1-P8: represent the reflection coefficients from the inputs of the different antenna arrays at the specific array operating channel, Sii. P9-P16: represent the transmission coefficients Sij, Sji representing two per pair of facing antenna arrays, where the transmission coefficient measured in relation to the facing antenna array channel. And P17-P25 represents the power received by each of the antenna arrays indirectly representing the gain.

In another embodiment, as shown in FIG. 4, the plurality of device antenna arrays 150 include a plurality of antenna arrays 152 with altered the spacing 158 between the array elements 152, the radiation patterns of the array elements are altered, and hence the sensitivities of the reflection and transmission parameters will cover alternate locations of the human body. In one embodiment, a first spacing 158a is about 3 mm. The array elements are equally spaced for the same array. In another embodiment, the spacing is not necessarily equal.

In the same embodiment, the spacings 158 will be changed to above or equal to the wavelength to create a plurality of grating lobes. The number of arrays 152 may be reduced to at least 4 in this instance. The number of elements per array may be also increased to at least 6 in the same embodiment, which will improve the gain. It is also possible that the spacing between the antenna array elements follow a certain distribution like chebychev, binomial, or butterworth or other distributions.

Figure 4A:
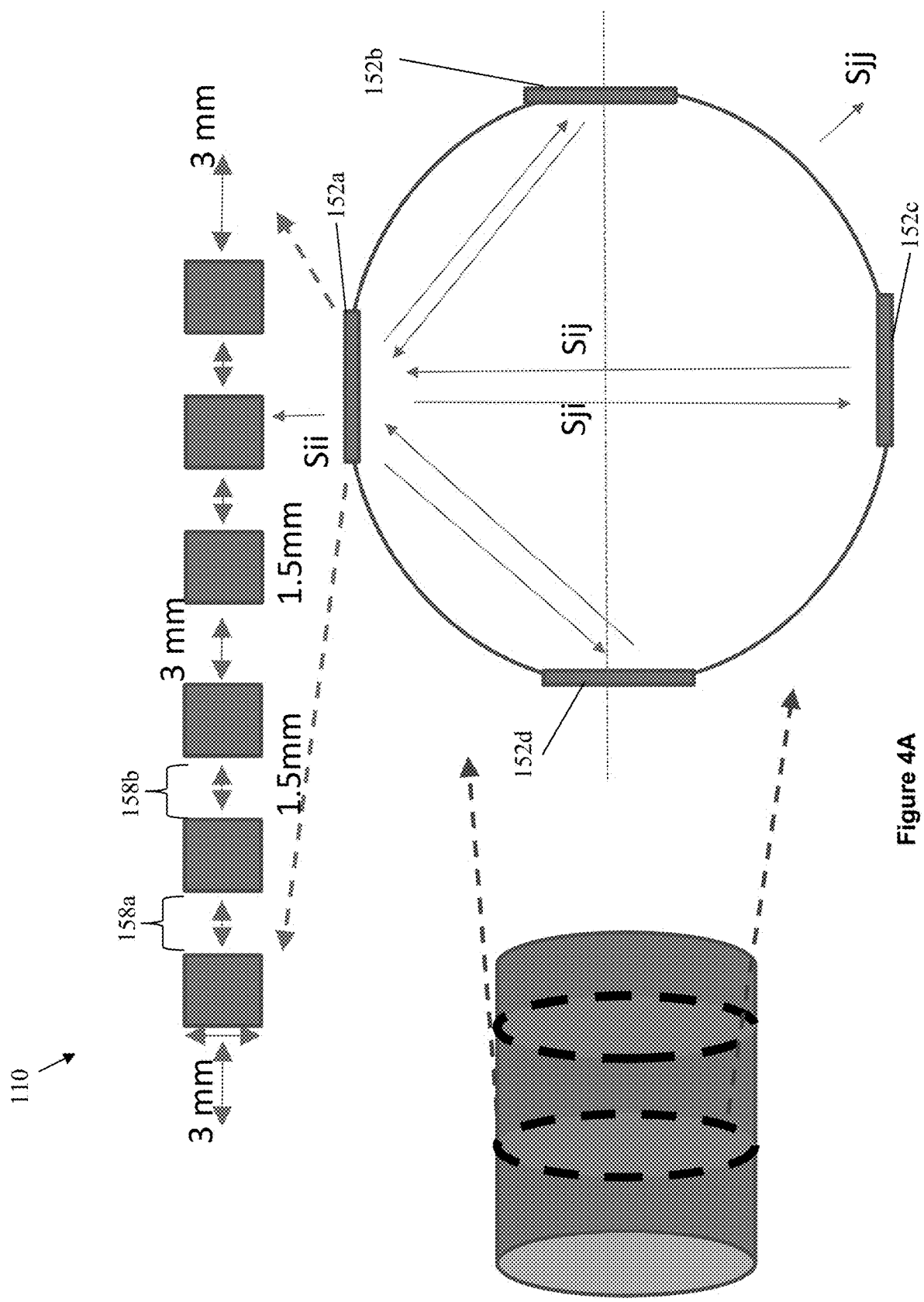
FIG. 4A is a schematic showing an mm-wave Antenna Arrays arrangement, according to one embodiment.

In alternate embodiment, phased arrays will be used for beam steering to cover different locations of the body. The following parameters are defined as follows. P26-P29: represent the reflection coefficients from the inputs of the different antenna arrays at the specific array operating channel, Sii. P30-P42: represent the transmission coefficients Sij, Sji representing two per pair of facing antenna array, as shown in FIG. 4A. 152a with b, c, d (6 params); 152b with c, d (4 params); and 152c with d (2 params). P43-P47: represents the power received by each of the antenna arrays indirectly representing the gain.

Figure 4C:
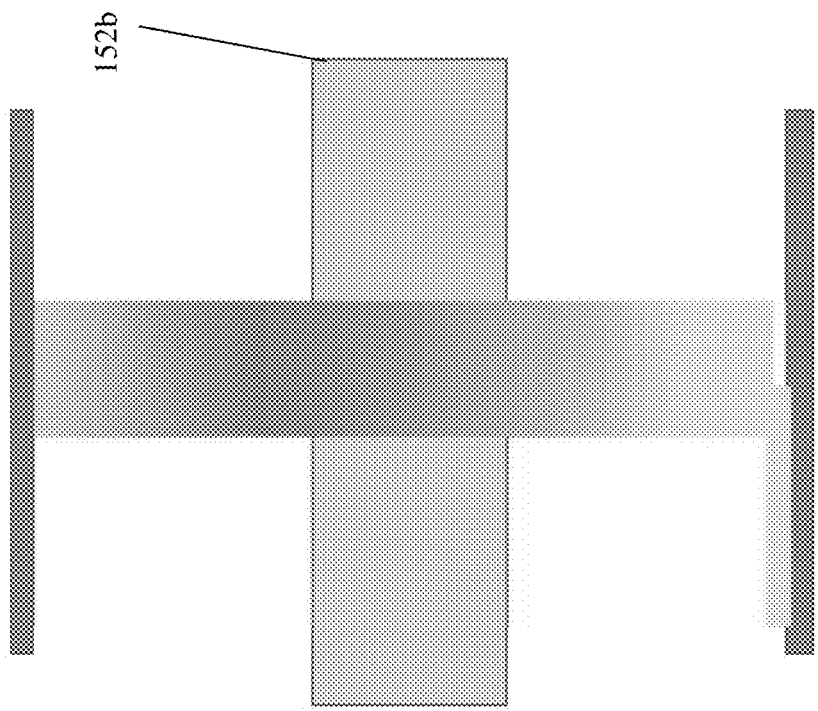
FIG. 4C is a schematic of the antenna equipped with an optical sensor to detect locations of dense capillary locations and depth, and hence the feedback can be used to detect phase necessary for beam steering and determining the necessary power level for different patients and locations of device. The vein detection sensor is to be used for subcutaneous vein detection, and can make use of image sensing and existing knowledge of the patient physiology to interpolate or estimate vein depth. This property preserves adaptivity of the design. The beam steering can be also used to obtain different readouts from the same antenna device.
Figure 4B:
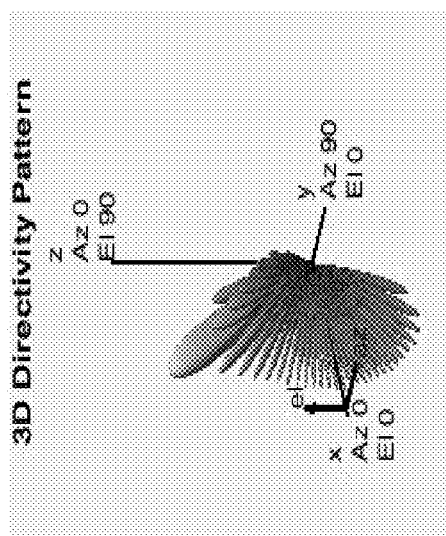
FIG. 4B is a graph showing the beam steering capability enables coverage of different spots.

FIG. 4B is a graph showing the beam steering capability enables coverage of different spots. FIG. 4C is a schematic of the antenna equipped with an optical sensor to detect locations of dense capillary locations, and hence the feedback can be used to detect phase necessary for beam steering.

Figure 4D:
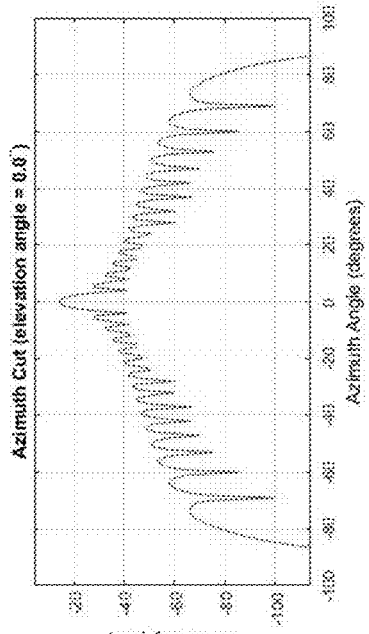
FIG. 4D is a top view of the array as a 30×30 URA planar array with rectangular grid.
Figure 4E:
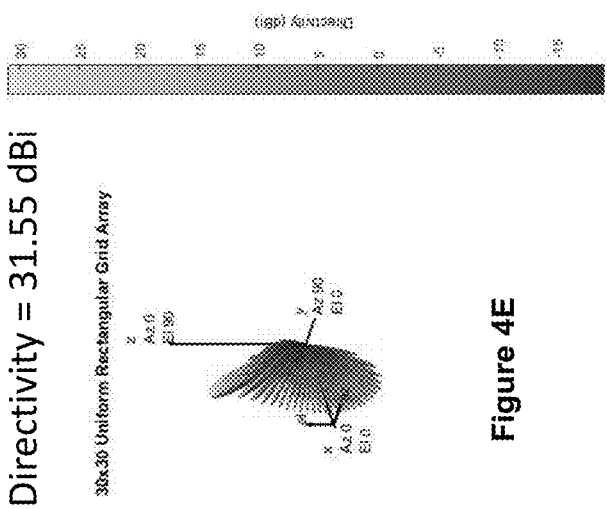
FIG. 4E is a graph showing the directivity is 31.55 dBi for the rectangular grid.
Figure 4G:
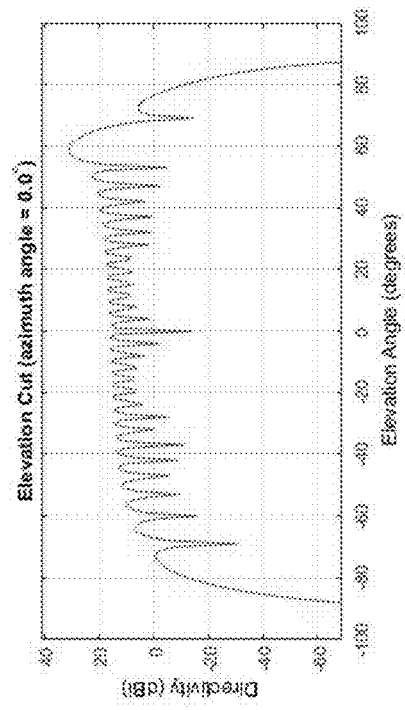
FIG. 4G is a graph for steering at angle $\theta=60$, $\phi=0$ for the elevation cut.
Figure 4F:
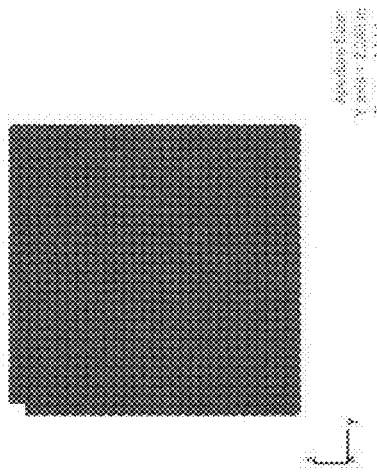
FIG. 4F is a graph for broadside steering ($\theta=0$, $\phi=0$) for an Azimuth Cut.

In one embodiment, an Array pattern for a Rectangular Array is shown in FIGS. 4D-4G. The array is a 30×30 URA planar array with rectangular grid as shown in FIG. 4D. The aperture size is about 2.248 mm for the y-axis, about 2.248 mm for the Z-axis, and the element spacing is about 74.949 mm for $\Delta y$ and about 74.948 mm for $\Delta z$. The directivity is about 31.55 dBi for the rectangular grid array as shown in FIG. 4E. The example for broadside steering ($\theta=0$, $\phi=0$) is shown in FIG. 4F for an Azimuth Cut. The Example for $\theta=60$, $\phi=0$ is shown in FIG. 4G for the elevation cut.

Figure 4H:
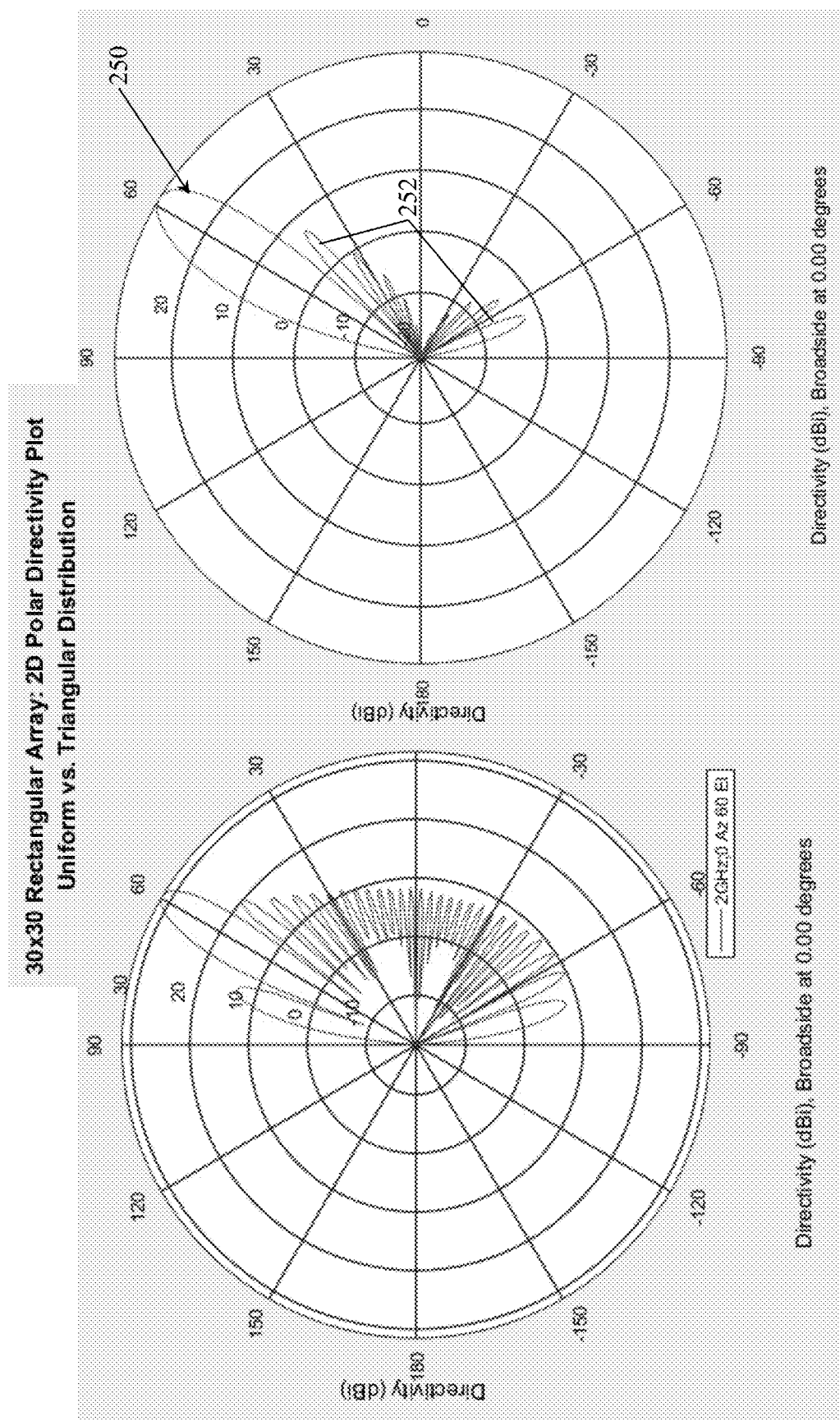
FIG. 4H is a 2D polar directivity plot showing an uniform vs. triangular distribution and directivity.
Figure 4J:
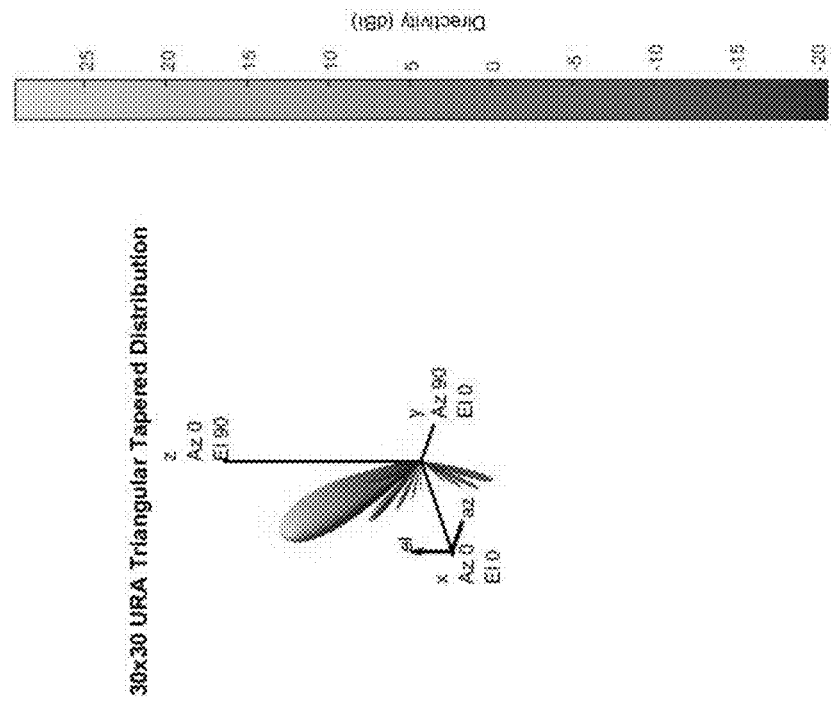
FIG. 4J is a graph showing the Triangular Tapered Distribution.
Figure 4I:
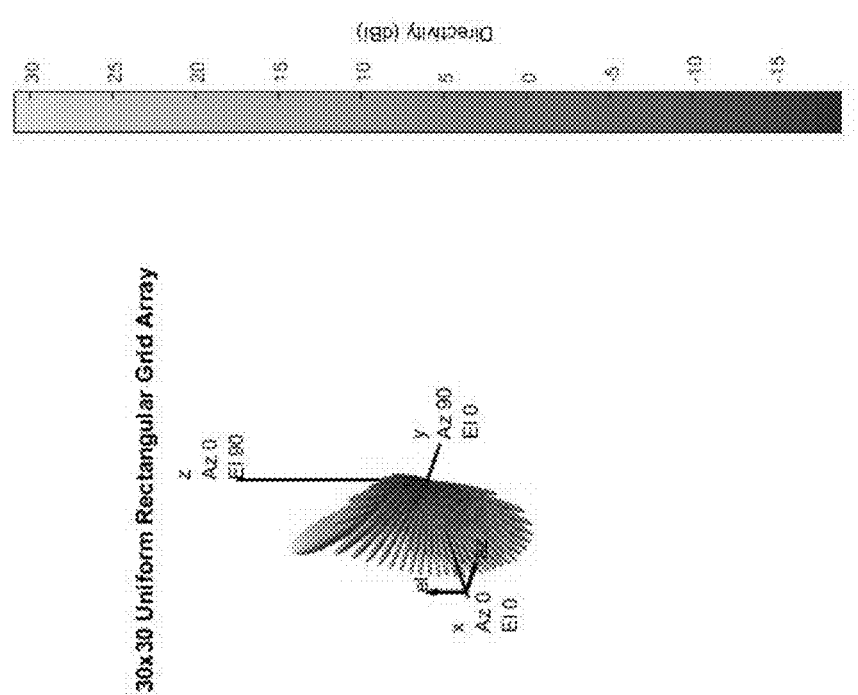
FIG. 4I is a graph showing the 3D Array Directivity for Uniform.

In one embodiment for optimal beam pattern, a triangular distribution 250 for minimum side lobes 252 is adopted, as shown in FIG. 4H. A 3D Array Directivity for Uniform distribution is shown in FIG. 4I and a Triangular Distribution is shown in FIG. 4J. The smallest side lobe levels for the triangular distribution 250.

Figure 4K:
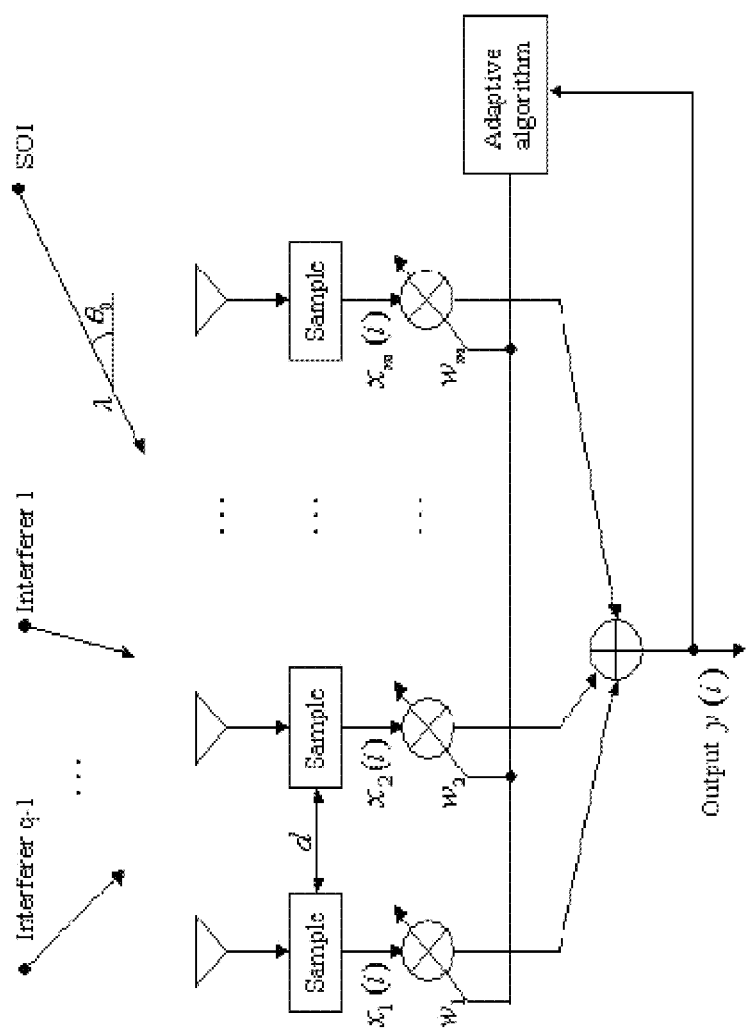
FIG. 4K is a schematic showing the Adaptive Uniform Linear Array structure given the position (x, y, z) of the target.

An Adaptive Algorithm Pseudo-code is disclosed. First, given the position (x, y, z) of the target, determine ($\theta_0$, $\phi_0$). Then, find the antenna $a_i$ and $(knd_x u_i)$ by relying on smart antenna adaptive beam steering algorithms, as shown in FIG. 4K showing the Example of Adaptive Uniform Linear Array structure [Ref: Wang, Lei. *Array signal processing algorithms for beamforming and direction finding*. Diss. University of York, 2009].

Figure 4L:
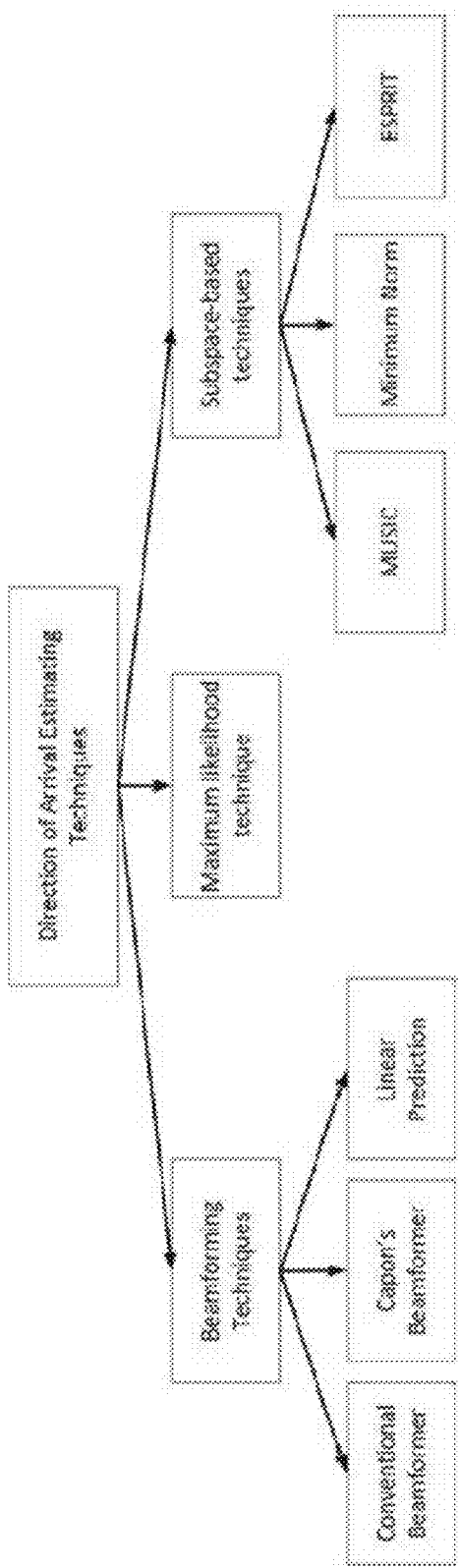
FIG. 4L is a flow chart showing the Direction of arrival estimation using antenna arrays.

Optimal Beam forming & Steering Algorithms is disclosed and uses new signal-processing algorithms often referred to as direction of arrival (DOA) algorithms. Muhamed, Rias. *Direction of arrival estimation using antenna arrays*. Virginia Polytechnic Institute and State University, 1996. Next, solve for the per-element characteristics (reconfigure antenna element pattern) to satisfy target beam steering based on user requirements to track certain directions and locations. Then, dynamically minimize interference and maximize intended signal reception. Different methods listed in FIG. 4L showing the Direction of arrival estimation using antenna arrays.

Figure 5:
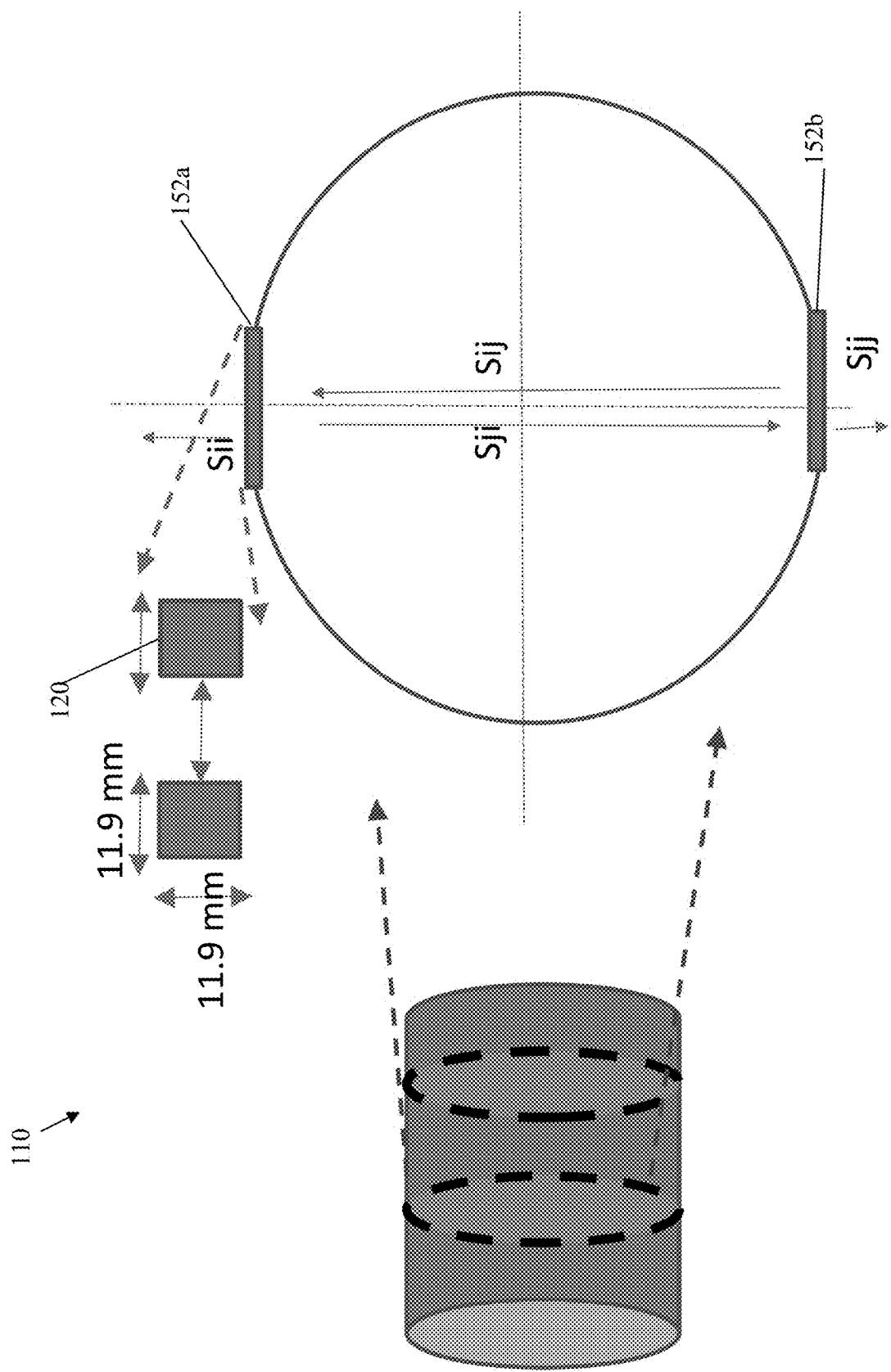
FIG. 5 is a schematic of the Micro-wave Antenna Arrays, according to one embodiment.

In another embodiment, the microwave antenna array operates at about 6 GHz, and has two elements allowing for 2 antenna arrays 152 to wrap around the human hand in the arrangement shown in FIG. 5. In the same embodiment the spacing between the antenna array elements is half wavelength enabling maximal transmission at a diametrically opposite antenna array.

The antenna arrays 152a and 152b operate at micro-wave range. Each antenna array operates at a different channel within the micro-wave. In one embodiment, the first antenna array 152 operates at one channel in the microwave range, for example 6 GHz, and the second antenna array 152b operates at the same channel for transmit/reflection parameters. In alternate embodiment, each element will receive a sweep of frequencies reflecting alternate channels with steps of 0.05 GHz for example. The antennas may be designed to operate at similar or different channels. In the latter only reflection coefficients may be retrieved based on the bandwidth.

Microstrip feeding can be used, or it can be coaxially fed. The feeding can be uniformly fed or it can follow a certain distribution. In microstrip feeding, a conducting strip is connected to the patch and therefore can be consider as extension of patch. In coaxial feeding, the outer conductor of the coaxial cable is connected to the ground plane, and the center conductor is extended up to the patch antenna.

Figure 6:
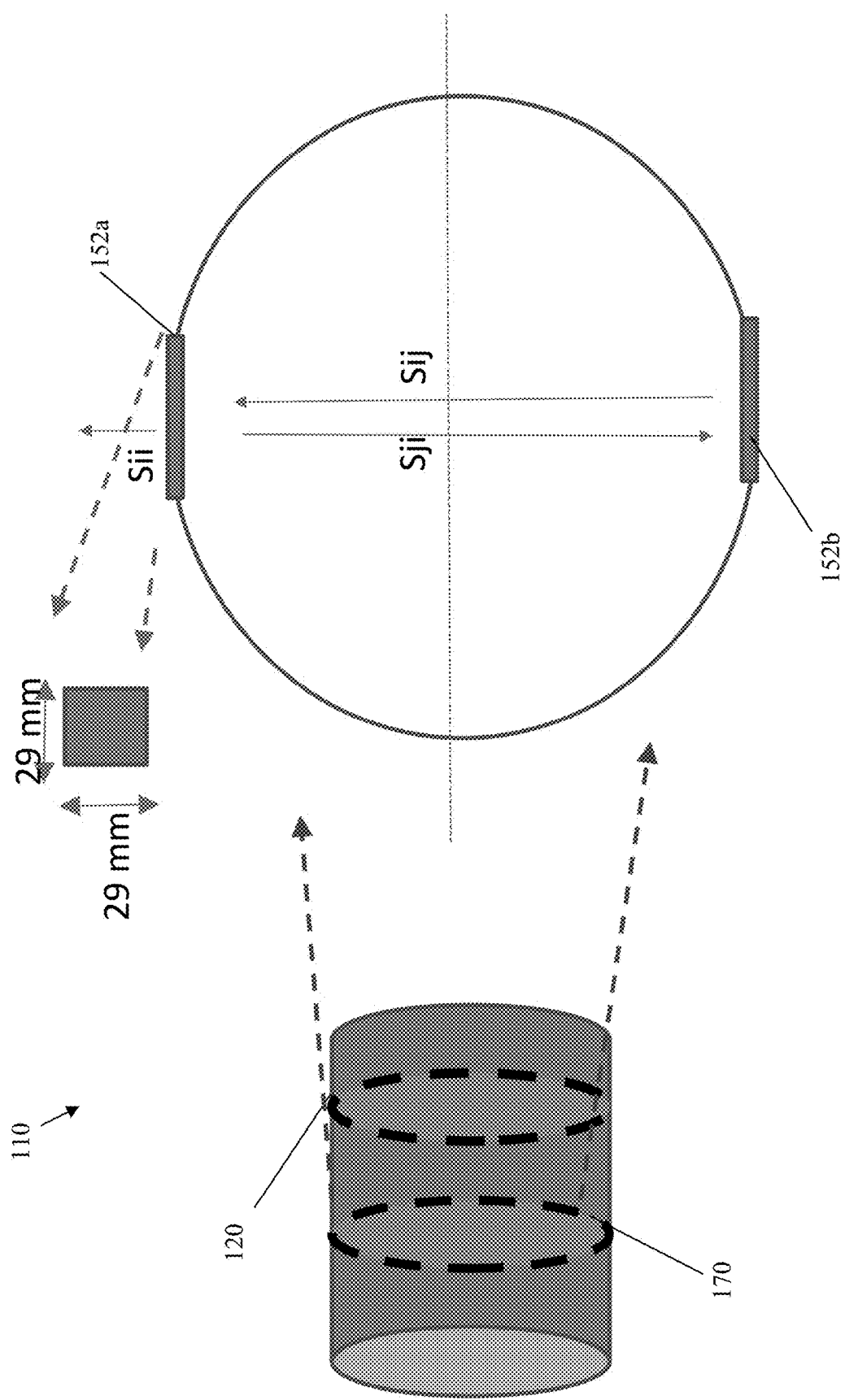
FIG. 6 is a schematic of the Micro-wave Antenna Arrays, according to one embodiment.

In one embodiment, the microwave antenna array operates at about 2.4 GHz, and has one element allowing for 2 antenna elements 152a and 152b to wrap around the human hand in the arrangement shown in FIG. 6. In the same embodiment, the spacing between the elements is half wavelength with maximal transmission at a diametrically opposite elements.

The antenna elements 152a and 152b operate at microwave and each element operates at a different channel within the micro-wave. In one embodiment, the two antenna elements 152a,b operate at about 2.4 GHz.

In one embodiment, a microstrip feeding can be used, or it can be coaxially or probe fed. The feeding can be uniformly fed or the feeding can follow a certain distribution.

In one embodiment, the following parameters are defined: P48-P49: represent the reflection coefficients from the inputs of the different antenna arrays at the specific array operating channel, Sii. P50-P51: represent the transmission coefficients Sij, Sji representing two per pair of facing antenna arrays, where the transmission coefficient measured in relation to the facing antenna array channel. P52-P53: represents the power received by each of the antenna arrays indirectly representing the gain.

Figure 7:
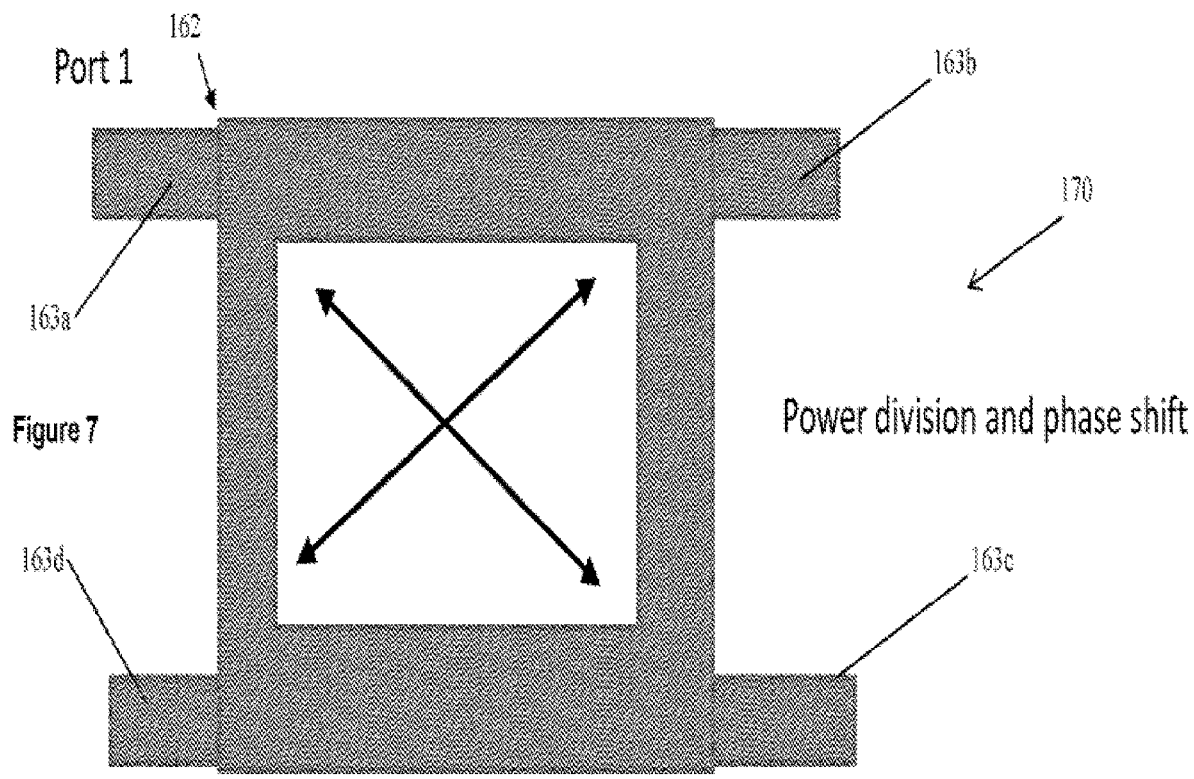
FIG. 7 is a schematic of the Detection-Directional Coupler.

As shown in FIG. 7, the coupler 162 comprises a first port 163a, a second port 163b, a third port 163c, and a fourth port 163d. The coupler 162 induces a phase shift and power division between a second port 163b and the third port 163c. The measured quantities in terms of phase shift and power division are function of the coupler medium.

Based on the dimensions as function of the wavelength, the reference phase shift can be varied, and multiple structures can be used to extract an averaged sensitivity. The coupler is implemented at both microwave, and mm-wave frequency. The following parameters are defined for the coupler (P60-P63; P64-P65). The phase and power division information are derived from each of the following measurements as follows: first port 163a and third port 163c are for coupling (S13); the third port 163c and the fourth port 163d are for directivity (S34); the first port 163a and the fourth port 163d are for isolation (S14); and the first port 163a and the second port 163b are for insertion loss (S12).

In one embodiment, a comparison between transmitted power at the second port 163b, and coupled power at the third port 163c in terms of phase and magnitude is obtained.

An array of loop antennas 154 is used to capture response in the UHF domain. The array of loop antennas 154 includes a distribution uniform or following specific distribution (yagi uda), and operates in UHF between about 100 MHz and about 1000 MHz. The array of loop antennas 154 includes between about 2-4 elements. And the following parameters are measured: P66 for the reflection coefficient for the whole array.

Figure 8:
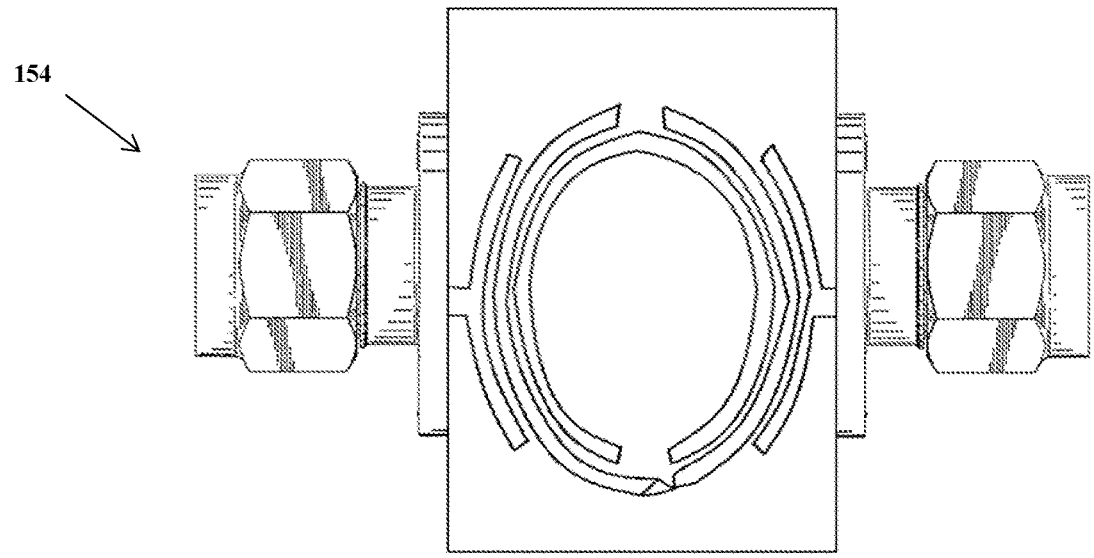
FIG. 8 is a top view of the Band Pass Filter.

As shown in FIG. 8, the bandpass filter 160 is used to indicate through a change in the frequency of operation, the variation of the glucose concentration in the blood stream. The filter 160 can be reconfigurable or tunable which will enable the sensing of the glucose changes over a variation of the frequency bands. The filter includes a structure such as cascaded reconfigurable filters. The filter includes an embodiment for the feeding that will be utilized to enable the special placement and adjust to human form (such as arm . . . etc.). In alternate embodiment, the filter can be bandstop, a cascade of bandstop and bandpass, or bank of such filters.

Resonators can also be used in the same manner as the filter whether standalone components or integrated within the filters structures.

The following parameters are measured by the filter: P67-P68: Reflection coefficient of the filter from both ports. P69-P70: transmission coefficient of the filter from both ports.

In one embodiment, a frequency dependent signal is applied to the filter 160. Based on the medium, the filter will pass the frequency component relevant to the effective medium properties given by for example equation (2):

$$Y = \Sigma_{i=1}^{N} a_i \sin(w_i t); \quad (2)$$

where $a_i$ represent an increasing magnitude, and where Glucose @w1 will sense power higher than @w2.

The level of sensed power will indicate operating frequency, and hence glucose level.

Figure 9:
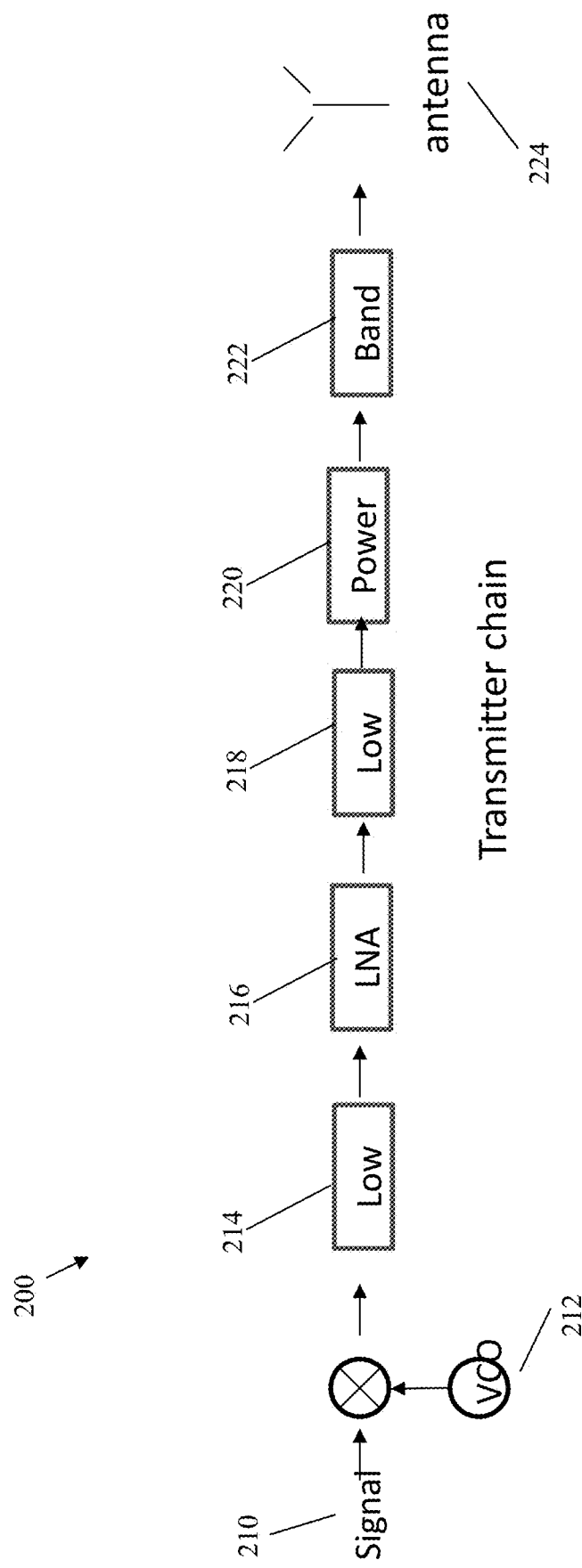
FIG. 9 is a schematic of the RF signal Generation to be fed to the device.

RF signal Generation 200 to be fed to devices is shown in FIG. 9. The signal 210 is coupled with a VCO 212 and then passes through a low pass filter 214, and then through an LNA 216, and then through a second Low pass filter 218, amplified with a power amplifier 220, filtered by a band pass filter 222, and then sent to the antenna 224. This implementation can be used for mm-wave designs or far-field measurements. For the design in the UHF and microwave, alternate embodiments will be used to address issues arising due to near field radiation. For example an integrated vector network analyzer can be incorporated in the system for s-parameter or power extraction.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Medical Embodiments

To validate the fabricated antenna 2 different approaches will be used: Blood mimicking materials (liquid) and Tissue mimicking materials: wet skin, fat, blood and muscles. Blood mimicking materials may include, but are not limited to: hemoglobin-based oxygen carriers (HBOC) and perfluorocarbon-based oxygen carriers (PFBOC). Tissue mimicking materials may include, but are not limited to: agar-based material or a gelatine-based material.

In both approaches the blood content will be modified to mimic what will happen in a disease state. For diabetes, different glucose indices will be used in combination with increased concentration of growth factors, lipids, antibodies, and especially drug used to treat diabetes and other related complications accompanying diabetes such as Insulin, statin, ascorbic acid, ACE inhibitors or ARBs, SGLT1 or SGLT2 inhibitors, etc. All of these additions will allow us to study the sensitivity of the designed antenna in the presence of different compound found in the human blood during the onset and the development of diabetes.

Importantly the tissue mimicking material is designed to allow continuous blood flow through the designed artificial tissue.

Example 2: Studies on Animal Models for Glucose Monitoring that can be Applied to Other Blood Markers and Tracers Animal Model Selection Murine and rodent models will be used for in vivo sensor performance evaluation.

Short term assessment: mice and rabbits will be employed permitting the evaluation of multiple sensors for short periods (post-prandial glucose levels and glucose assessment up to 2 days).

Long term assessment: Pigs that more accurately represent human tissue physiology will be used to obtain accurate sensor performance data for long-term assessment.

To assess the sensors accuracy performance, animals will be divided into different groups depending on the disease state.

For diabetes the following groups will be used:

Group 1: Healthy animals; Group 2: Healthy animals, where blood glucose levels will be artificially altered to achieve glucose concentrations outside of the euglycemic range; Group 3: Diabetic animals; Group 4: Diabetic animals treated with insulin to achieve glucose concentration inside of the euglycemic range; Group 5: Diabetic animals treated with different oral hypoglycemic (i.e. metformin, SGLT2 inhibitors, etc.); Group 6: Diabetic animals treated with oral hypoglycemic and statin; Group 7: Diabetic animals treated with oral hypoglycemic and hypertensive drugs; and Group 8: Diabetic animals treated with combination of drugs.

Example 3: Clinical Trials

For human antenna/sensor performance evaluation the inclusion and exclusion criteria will be set based on the recommendations set by the American Diabetes Association (ADA), the National Institute of Health (NIH), the Montreal Cognitive Assessment (MOCA), etc., clinical trials standards, (example patients with cognitive impairment will be excluded, patients with respiratory difficulties will be excluded, etc.)

Healthy subjects, patients with type 1 and patients with type 2 diabetes will be recruited. Follow up using standard invasive glucometer as well as medical testing of HBA1C, lipid profile, etc. will be used.

Glucose readings will be obtained from both a glucometer (finger prick readings) and from the developed non-invasive glucose sensor to assess how the non-invasive glucose sensor measurements correlate with glucometer readings. 5 to 6 measurements will be recorded daily: (1) Fasting, (2) postprandial glucose (1.5 to 2 hours after consuming a meal), (3) 2 to 6 hours after insulin injection and (4) before and (5) after 30-45 minutes of moderate exercise.

The groups of the study are divided based on different criteria: Healthy control; Diabetic patients with standard control of their glucose levels; Diabetic patients with strict control of their glucose levels (HbA1C less then 6.5); PS: medications (Ace inhibitors, ARBs, statins, etc.); and smoking status will be taken into account in the analysis of the data.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A Monitoring Device comprising: a body area network operably coupled to a plurality of device antenna arrays; the body area network comprised of a plurality of sensors; the plurality of sensors and the plurality of device antenna arrays include a central processing unit for creating and monitoring signals; the plurality of sensors and the plurality of device antenna arrays are connected wirelessly each other and to the central processing unit; the central processing unit processes all signals received from the plurality of sensors and the plurality of device antenna arrays; the plurality of device antenna arrays operate at a mm-wave range, a UHF, or a microwave range; the plurality of device antenna arrays further comprises a filter element and a coupler including a functionality sensitive to a medium.

2. The Monitoring device of claim 1, wherein the plurality of device antenna arrays comprise a plurality of circular antenna arrays; the plurality of circular antenna arrays is arranged in circular fashion; the plurality of circular antenna arrays further comprises a first circular array, a second circular array, and a third circular array; wherein the first circular array operates at the microwave range, the second circular array operates at the mm-wave range, and the third circular array operates at a UHF range.

3. The Monitoring device of claim 2, wherein a spacing between the at least three elements of the plurality of device antenna arrays is about a half wavelength; and the plurality of device antenna arrays further comprises an array of loop antennas at a UHF range;

the plurality of device antenna arrays includes circular antenna arrays operating at about 60 GHz that are configured to wrap around an anatomical limb.

4. The Monitoring device of claim 3, wherein the antenna arrays operate at mm-wave and each antenna array operates at a different channel within the mm-wave.

5. The Monitoring device of claim 3, wherein the plurality of device antenna arrays are diametrically opposite, transmit signals to each other, and operate at the same channel, leading to at a plurality of exclusive channels.

6. The Monitoring device of claim 3, wherein the at least three elements that are neighboring transmitting/receiving array capture a coupled electromagnetic field.

7. The Monitoring device of claim 6, wherein the plurality of device antenna arrays are uniformly fed and the plurality of device antenna arrays reflection and transmission parameters are captured comprising P1-P8: represent a reflection coefficients from an input of the different antenna arrays at the specific operating channel, Sii; P9-P16: represent a transmission coefficients Sij, Sji representing the total transmitted signals comprising the diametrically opposite element pairs, where a transmission coefficient is measured in relation to a facing antenna array that operates at the same channel.

8. The Monitoring device of claim 2, the plurality of device antenna arrays include a plurality of antenna arrays with an altered spacing between the array elements of the plurality of device antenna arrays, a plurality of radiation patterns of the array elements are altered, and the plurality of sensitivities of the reflection and transmission parameters cover alternate locations of the human body when the measurement is made.

9. The Monitoring device of claim 2, wherein the 4 plurality of device antenna arrays include a plurality of antenna array elements at a spacing at least equal to or greater than half the wavelength; the spacing for a first antenna array element is equal to half wavelength and the spacing for a second antenna array element is equal to one wavelength or above resulting in different radiation patterns and grating lobes of the plurality of antenna array elements, the plurality of sensitivities of the reflection and transmission parameters cover alternate locations of the human body when the measurement is made.

10. The Monitoring device of claim 1, the plurality of antenna arrays include one or more multiple phased antenna arrays with a radiation beam that are used for beam steering to cover different locations of the body;

and the one or more multiple phase antenna arrays are arranged in a circular fashion, and each phased array pair operate at a specific frequency creating a channel; the phase antenna arrays reflection and transmission parameters are captured comprising a second distribution parameters are defined as follows: P26-P29: represent the reflection coefficients (Sii) from the inputs of the different phased antenna arrays at the specific array operating channel, P30-P42: represent the transmission coefficients Sij, Sji representing two per pair of phased antenna array, with b, c, d (6 params); 152b with c, d (4 params); and 152c with d (2 params).

11. A method of monitoring comprising:

operably coupling a body area network to a plurality of device antenna arrays; the body area network comprised of a plurality of sensors and the plurality of device antenna arrays targeting multiple locations on the body, creating and monitoring signals from the plurality of sensors and plurality of device antenna arrays by a central processing unit operably coupled with the plurality of sensors and the plurality of device antenna arrays; connecting plurality of sensors and plurality of device antenna arrays wirelessly to each other and to the central processing unit; processing all signal information received from the plurality of sensors and the plurality of device antenna arrays by the central processing unit;

operating the plurality of device antenna arrays at a UHF, a microwave range, or a mm wave range;

including a filter element and a couple with a functionality sensitive to a medium.

12. The method of claim 11, further comprising arranging the plurality of circular antenna arrays in a circular fashion operating at the UHF, the microwave range, or the mm-wave range.

13. The method of claim 12, further comprising arranging an array of loop antennas arrays at the UHF range and the circular antenna arrays operating at about 60 GHz that wrap around an anatomical limb.

14. The method of claim 13, further comprising spacing the antenna array elements at about a half wavelength, and operating the antenna arrays at mm-wave and operating each antenna array at a different channel within the mm-wave.

15. The method of claim 14, further comprising placing the antenna array elements diametrically opposite where facing elements transmit signals to each other, operate at the same channel, leading to a plurality of exclusive channels.

16. The method of claim 12, further comprising coupling the electromagnetic field between the elements that are neighboring transmitting/receiving array signals.

17. The method of claim 16, further comprising uniformly feeding the array elements and capturing the array elements reflection and transmission parameters comprising P1-P8: representing the reflection coefficients from an input of the different antenna arrays at the specific operating channel, Sii; P9-P16:

represent the transmission coefficients Sij, Sji representing the total transmitted signals comprising the diametrically opposite element pairs, where the transmission coefficient is measured in relation to the facing antenna array element and that operates at the same channel.

18. The method of claim 17, further comprising altering the spacing between the plurality of antenna array elements of a plurality of antenna arrays, altering the radiation patterns of the array elements, and covering alternative locations of the human body with the sensitivities of the reflection and transmission parameters.

19. The method of claim 18, further comprising creating the spacing for one array to be equal to half wavelength and the spacing another array to be equal to one wavelength or above resulting in different radiation patterns and grating lobes of the array elements, and covering different sensitivities of the reflection and transmission parameters that cover alternate locations of the human body.

20. The method of claim 18, further comprising arranging the phased arrays in a circular fashion, and each phase array pair operates at a specific frequency creating a channel; the plurarlity of antenna arrays include one or more multiple phase antenna arrays with a radiation beam that can cover different locations of the body;

and the phased array reflection and transmission parameters are captured comprising a second distribution parameters as follows: P26-P29: represent the reflection coefficients (Sii) from the inputs of the different antenna arrays at the specific array operating channel, P30-P42: represent the transmission coefficients Sij, Sji representing two per pair of facing antenna array, with b, c, d (6 params); 152b with c, d (4 params); and 152c with d (2 params);

and P43-P47: represents the power received by each of the antenna arrays indirectly representing the gain, wherein the optimal beam pattern is a triangular distribution including minimum side lobes.

* * * * *